Figure 1:
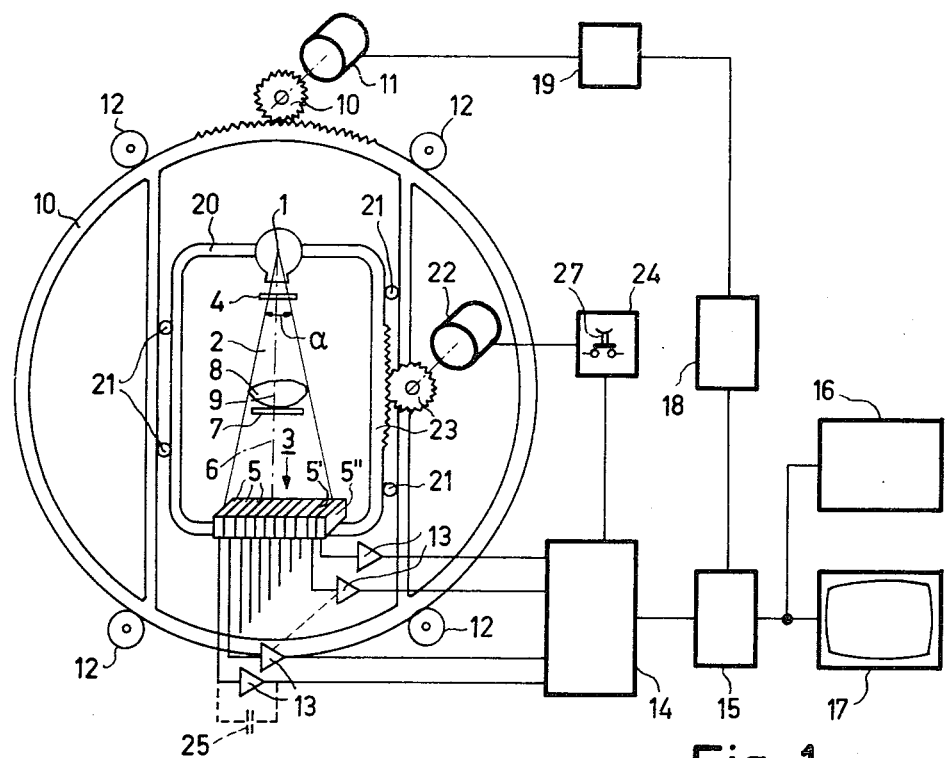

United States Patent [19]

Albrecht et al.

[11] 4,292,524
[45] Sep. 29, 1981

[54] EXAMINING DEVICE FOR DETERMINING LOCAL ABSORPTION VALUES IN A SLICE OF A BODY

[75] Inventors: Cornelius B. J. d. Albrecht; Jan J. M. Mulleneers, both of Eindhoven, Netherlands

[73] Assignee: U.S. Philips Corporation, New York, N.Y.

[21] Appl. No.: 948,736

[22] Filed: Oct. 5, 1978

[30] Foreign Application Priority Data

Oct. 14, 1977 [NL] Netherlands ........................ 7711285

[51] Int. Cl.² .............................................. A61B 6/00
[52] U.S. Cl. ................................ 250/445 T; 250/360
[58] Field of Search ............................ 250/445 T, 360

Primary Examiner—Alfred E. Smith
Assistant Examiner—T. N. Grigsby

Attorney, Agent, or Firm—Thomas A. Briody; Robert T. Mayer; Jack E. Haken

[57] ABSTRACT

In transversal tomography devices in which the X-ray beam and the array of detectors are such that they cover the higher slice to be examined, a very large array dynamic range (the ratio between the largest detector signal and the smallest detector signal occurring during a measurement) occurs. The array dynamic range often lies between the values $10^4$ and $2.10^4$. By adaptation of integration capacitances of the integrators connected to the detectors to the position of the detector in the array, the array dynamic range can be reduced. If the ratio between the largest integration capacitance (at the end of the row) and the smallest integration capacitance (in the center of the array) equals, for example, 40, the array dynamic range is substantially smaller than 1000. The advantage consists in that less severe requirements are imposed on the signal processing section connected to the integrators.

6 Claims, 3 Drawing Figures

EXAMINING DEVICE FOR DETERMINING LOCAL ABSORPTION VALUES IN A SLICE OF A BODY

The invention relates to an examining device for determining local absorption values in a slice of a body, comprising a radiation source for generating a beam of radiation which irradiates the body, radiation direction means for irradiating the slice in a number of different directions, the direction of the radiation being situated in the slice to be examined, and an array of detectors which covers the entire beam and which serves for converting the radiation emerging from the body into electrical measuring values. An examining device of this kind is disclosed in U.S. Pat. No. 3,937,963. In a device of this kind, the array of detectors comprises of from 150 to 300 detectors which are adjacently arranged along a sector of a circle having a radius of approximately one meter. For the use of the examining device, two kinds of dynamic range of the measuring signals must be distinguished. The ratio between the largest and the smallest measuring signal measured by an individual detector is a first ratio which will be referred to hereinafter as the individual dynamic range. The ratio between the largest and the smallest measuring signal occurring during a measurement is a second ratio which will be referred to hereinafter as the array dynamic range. In examining devices which form the subject of the present invention, the individual dynamic range has an order of magnitude of 100, whilst the array dynamic range has an order of magnitude of 10,000. Such a wide array dynamic range imposes problems as regards the processing of the measuring signals.

A known method of reducing the array dynamic range is the use of an attenuating body which may be, for example, a water bag which is arranged around the body to be examined, for example, as described in U.S. Pat. No. 3,937,963. This water bag solves the dynamic range problem, but the bag is uncomfortable for the patients examined by means of the device, and also for the examiner.

The attenuating body may alternatively be a so-termed compensation filter which is arranged between the radiation source and the body to be examined. A compensation filter of this kind is described in the U.S. Pat. No. 3,937,963. However, in view of the limited space available, a compensation filter must be small, so it must be made of a material having a comparatively high effective atomic number. However, local hardening of the radiation then occurs, which necessitates a correction of the measuring signal which is dependent of the location of the associated detector. Filters made of a material having a comparatively low atomic number do not have the latter drawback. However, the use of a compensation filter imposes a further difficulty in that calibration of the detectors with a filter other than the compensation filter must be performed. Any small inaccuracy as regards the position of the filters to be consecutively used will then cause correlated measuring errors which give rise to circular faults in the display of the calculated absorption image.

The invention has for its object to reduce the array dynamic range of the device in a simple manner, whilst eliminating the described attenuating bodies.

To this end, the device in accordance with the invention is characterized in that it comprises amplifier circuits, each of which is connected to a detector, a sensitivity of an amplifier circuit associated with a detector which is situated in or in the vicinity of a centre of the array of detectors being higher than a sensitivity of an amplifier circuit which is connected to a detector at or in the vicinity of an end of the array of detectors. As a result of the fact that the sensitivity of the amplifier circuit is dependent of the position of the associated detector in the array of detectors, the array dynamic range is reduced so that the further processing of the measuring signals is substantially simplified. Use is made of the fact that the radiation which is detected by the detectors in and in the vicinity of the centre is attenuated more than the other radiation. As a result, the amplifier circuits connected to the detectors situated at the end of the array need be less sensitive than the other amplifier circuits.

An embodiment of the examining device in accordance with the invention in which the amplifier circuits comprise integrators is characterized in that integration capacitances associated with a first group of detectors which are situated in and in the immediate vicinity of the centre of the array all have the same value k, whilst integration capacitances associated with two third-groups of detectors which are each situated at the end of the array all have the same but higher value l, integration capacitances associated with two second groups of detectors which are each situated between the first and a third group of detectors having a value which increases from the value k to the value l in accordance with a geometrical series, viewed from the first group in the direction of a third group. This embodiment has been found to be attractive, because the further processing of the measuring signals of the first group and of the two third groups of detectors required taking into account of only one factor which indicates the difference in integration capacitance between the integrators associated with the first and the third group.

It has been found that a quotient of the values l and k of the integration capacitances is preferably larger than 16 and smaller than 64. The array dynamic range thus remains smaller than 1000, the signal/noise ratio not being adversely affected thereby.

A preferred embodiment of a device in accordance with the invention is characterized in that the radiation source and the array of detectors are arranged to be rotatable together around an axis of rotation which is situated between the radiation source and the array of detectors, a distance being adjustable between the radiation source and the axis of rotation, a distance between the radiation source and the array of detectors remaining constant. In a device of this kind, optimum use can be made of the reduction of the array dynamic range by the adaptation of the sensitivity of the amplifier circuits, because as a result of the displacement of the radiation source with respect to the axis of rotation, a body to be examined is positioned so that its position is adapted to the position-dependent sensitivity of the amplifier circuits.

The invention will be described in detail hereinafter with reference to the accompanying diagrammatic drawing.

Figure 2:
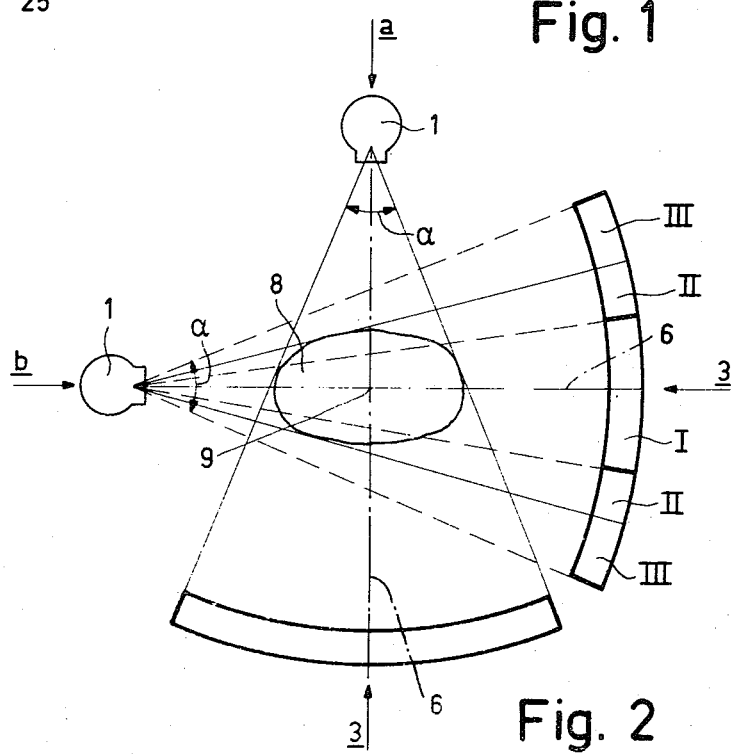
Figure 3:
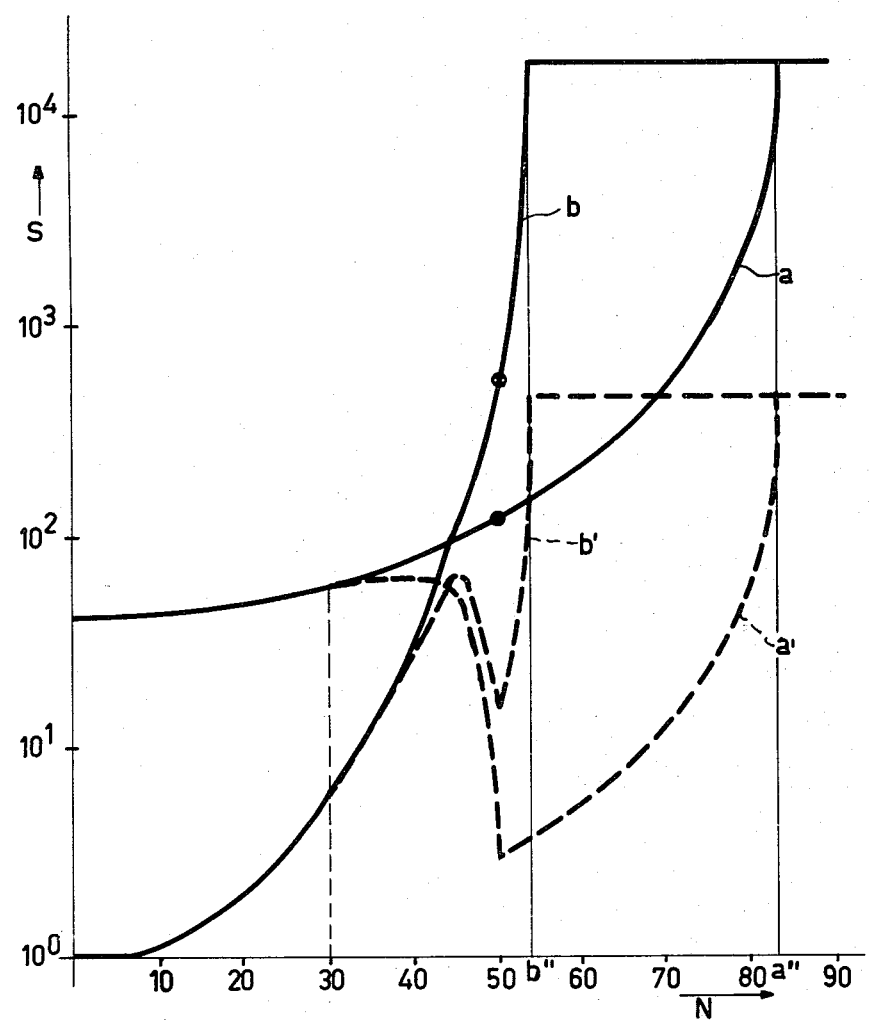

FIG. 1 diagrammatically shows a device in accordance with the invention,

FIG. 2 shows a part of a connection circuit for the array of detectors of a device as shown in FIG. 1, and FIG. 3 shows a diagram in which the relative sensitivity of the detectors is shown as a function of the position occupied in the array of detectors.

An X-ray examining device as diagrammatically shown in FIG. 1 comprises a radiation source 1 which preferably consists of an X-ray tube, but which may alternatively be a radioactive isotope having an effective, natural radiation such as Am241 or G153. The intensity of an X-ray beam 2 to be emitted by the radiation source 1 is locally measured by an array of detectors 3. The radiation source 1 forms a fan-shaped beam having an angle of aperture $\alpha$. The beam 2 is at least in principle parallel in a direction perpendicular to the plane of the drawing and has a small thickness of, for example, from 3 to 15 mm in this direction. A slit-shaped aperture 4 is provided in order to form such a beam. The width dimension of the detectors 5 and their spacing (in the direction of the array of detectors 3) determines the number of detectors in the beam 2 and hence the resolution within a given beam angle. The array of detectors 3 is composed of, for example, 300 detectors with a centre-to-centre distance of a few millimeters. Alernatively, use can be made of an elongate ionisation chamber which is filled with a rare gas and in which an array of individually arranged, locally detecting electrodes are provided. The array of detectors 3 is symmetrically arranged with respect to a beam centre 6. The examining device furthermore comprises a supporting table 7 for a body 8 to be examined which is displaceable along an isocentric axis 9. The isocentric axis 9 intersects the beam centre 6. The system formed by the X-ray source 1 and the array of detectors 3 is rotatable around the body 8 by means of a toothed ring 10 which is driven by a motor 11 and which is supported and guided by bearings 12. The rotation of the system formed by the X-ray source 1 and the array of detectors 3 may be continuous as well as intermittent. In the latter case, a rotation step is performed after each measurement. The measuring signals of the detectors 5 are applied, via amplifiers 13, to a signal converter 14 which comprises, for example, a multiplex circuit and an analog-to-digital converter. The converted signals are applied to an arithmetic device 15. A counter 18 counts the number of signals applied to the arithmetic device 15 per measurement. When a counting position of the counter 18 corresponding to the number of detectors 5 is reached, a control circuit 19 for driving the motor 11 is activated for a brief period of time. The ring 10 is then rotated, after which a subsequent measurement is performed. The arithmetic device 15 calculates, on the basis of the signals from all measurements, stored, for example, in a memory 16, the local absorption values which are then displayed on a display device 17. If desired, the calculated absorption values can also be stored in the memory 16. Each detector 5 has coupled to it an amplifier 13 which, in accordance with the invention, has a sensitivity adapted to the position of the associated detector 35 in the array 3. Alternatively, the amplifier 13 may operate as an integrator in accordance with the invention. This is denoted by a dotted line in the Figure. The value of the integrator capacitance 25 is then adapted to the position of the detector 5 in the array 3.

An example of such an adaptation will be described with reference to FIG. 2. This Figure shows two positions a and b which can be occupied by the system formed by the X-ray source 1 and the array of detectors 3 with respect to the body 8 during measurements. The body 8 to be examined usually has an ellipsoid section, the ratio between the long axis and the short axis being approximately 5/3. For the example to be described it is assumed that the body 8 consists of an homogeneous material having the same absorption behaviour as water. In the position b, a series of measuring values has been determined by means of the system formed by the X-ray source 1 and the array of detectors 3, the measuring value determined along the long axis of the body 8, coinciding with the beam centre 6, having been assigned a relative value 1. The other measuring values have been related thereto. The relative values S are shown in a graph in FIG. 3. The values S are plotted as a function of the position N of a detector in the array 3 and form the curve b. It is assumed that the array 3 comprises 180 detectors which are symmetrically arranged with respect to the beam centre 6. Therefore, N comprises 90 positions in the graph. The graph shows that the array dynamic range is larger than $10^4$.

A second series of measuring values, determined in the position a of the system formed by the X-ray source 1 and the array of detectors 3, are also related to the measuring value determined in the beam centre 6 in the position b. The relative measuring values are plotted in the graph of FIG. 3 and form the curve a. It is clearly shown that the array dynamic range is substantially smaller in this position and has a value of 600.

In order to reduce the array dynamic range, the integration capacitance of the integrators connected to the detectors is adapted to the position of the detectors in the array 3 as follows. A first group of detectors, denoted by the reference I in FIG. 2, is connected to integrators having an integration capacitance of a relative value 1. Two third groups of detectors, denoted by the reference III in FIG. 2, are connected to integrators having an integration capacitance having a relative value 40. Each of the two second groups of detectors, denoted by the reference II, is situated between the group I and one of the groups III and is connected to integrators which have an integration capacitance which increases in accordance with a geometrical series from the group I in the direction of the group III, their relative value increasing from 1 to 40.

The graph of FIG. 3 also shows the relative measuring values measured in the positions a and b by means of the array of detectors and the adapted integrators. The stroke-dot curves a' and b' represent the relative measuring values determined in the positions a and b, respectively. In the example, the detectors 1 to 30 belong to the group I, the detectors 31 to 50 belong to the group II and the further detectors form part of the group III. The number of detectors of the group III is chosen so that the radiation of the beam having an angle of aperture $\alpha$ which does not pass through the body 8 in the position b is measured by the detectors of the group III. Furthermore, the number of detectors of the group I is chosen to be so large that the dynamic range within the group I is smaller than 10, for which adaptation is not required. It is clearly shown that adequate adaptation of the sensitivity of the amplifiers connected to the detectors or of the integration capacitances of the integrators associated with the detectors can reduce the array dynamic range from the high value exceeding $10^4$ to a value smaller than 500.

In order to enable optimum use of the adaptation for reducing the array dynamic range also in the case of measurements performed on small objects, the distance between the X-ray source 1 and the body 8 to be examined is preferably adjustable. As is shown in FIG. 1, therefore, the X-ray source 1 and the array of detectors 3 are mounted on a frame 20 which is displaceable along guides 21 within the ring 10. The frame 20 is displaced by means of an electric motor 22, via a rack and pinion device 23. A control circuit 24 for the motor 22 can be operated, for example, by means of a manual switch 27, but use can alternatively be made of the two measuring values of the two outer detectors 5' and 5". Prior to the start of a measurement, the measuring values of the two detectors 5' and 5" are applied to the control circuit 24 via the signal converter 14, the frame 20 then being displaced so that the measuring value of the detector 5" is maximum and the measuring value of 5' is lower. The detector 5" then measures X-radiation which just passes besides the body 8, whilst the detector 5' measures X-radiation which passes through the body 8.

What is claimed is:

1. An examining device for determining local absorption values in a slice of a body, comprising a radiation source for generating a beam of radiation which irradiates the body, radiation direction means for irradiating the slice in a number of different directions, the radiation beam being situated in the slice to be examined, and an array of detectors which covers the entire beam and which serves for converting the radiation emerging from the body into electrical measuring values, characterized in that the examining device further comprises amplifier circuits, each of which is connected to a detector, a sensitivity of an amplifier circuit associated with a detector which is situated in or in the vicinity of the centre of the array of detectors being higher than a sensitivity of an amplifier circuit which is connected to a detector at or in the vicinity of an end of the array of detectors.

2. A device as claimed in claim 1, characterized in that the amplifier circuits associated with a first group of detectors, being situated in or in the direct vicinity of the centre of the array of detectors, all have the same gain factor m, the amplifier circuits associated with two second groups of detectors, adjoining the first group, having a gain factor which decreases from m to n in accordance with a geometrical series, the amplifier circuits associated with two third groups of detectors, adjoining the second groups of detectors, all having the same gain factor n.

3. An examining device as claimed in claim 1, characterized in that each of the amplifier circuits comprises an integrator with an integration capacitance which has a value dependent on the position of the detector associated with the integrator, the integration capacitances associated with the detectors in the centre of the array being smaller than the integration capacitances associated with the detectors at the end of the array.

4. An examining device as claimed in claim 3, characterized in that the integration capacitances associated with a first group of detectors, being situated in and in the direct vicinity of the centre of the array, all have the same value k, the integration capacitances associated with two third groups of detectors, each of which are situated at the end of the array, all having the same value 1, the integration capacitances associated with two second groups of detectors, each of which is situated between the first and the third group of detectors, having a value which increases from the value k to the value 1 in accordance with a geometrical series, from the first group in the direction of the third group.

5. An examining device as claimed in claim 4, characterized in that a quotient of the values 1 and k respectively, is smaller than 16 and larger than 64.

6. An examining device as claimed in any one of the preceding claims, characterized in that the radiation source and the array of detectors are arranged to be rotatable together about an axis of rotation which is situated between the radiation source and the array of detectors, a distance between the radiation being adjustable source and the axis of rotation, a distance between the radiation source and the array of detectors then remaining constant.

* * * * *

UNITED STATES PATENT AND TRADEMARK OFFICE
CERTIFICATE OF CORRECTION

PATENT NO. : 4,292,524
DATED : September 29, 1981
INVENTOR(S) : CORNELIUS B.J.D. ALBRECHT ET AL It is certified that error appears in the above—identified patent and that said Letters Patent is hereby corrected as shown below:

Claim 6, Line 6, Line 7, delete "being adjustable".

Claim 6, line 7, after "rotation" insert --being adjustable--.

Signed and Sealed this

Twelfth Day of October 1982

[SEAL]

Attest:

GERALD J. MOSSINGHOFF

Attesting Officer     Commissioner of Patents and Trademarks